United States Patent
Yamaguchi et al.

(10) Patent No.: US 10,526,636 B2
(45) Date of Patent: *Jan. 7, 2020

(54) METHOD FOR DETERMINING WHETHER OR NOT TEST SAMPLE CONTAINS PHYTOPATHOGENIC FUNGUS

(71) Applicant: Panasonic Intellectual Property Management Co., Ltd., Osaka (JP)

(72) Inventors: Kaori Yamaguchi, Fukui (JP); Yoshitsugu Uriu, Osaka (JP)

(73) Assignee: PANASONIC INTELLECTUAL PROPERTY MANAGEMENT CO., LTD., Osaka (JP)

( * ) Notice: Subject to any disclaimer, the term of this patent is extended or adjusted under 35 U.S.C. 154(b) by 0 days.

This patent is subject to a terminal disclaimer.

(21) Appl. No.: 15/844,627

(22) Filed: Dec. 18, 2017

(65) Prior Publication Data

US 2018/0208960 A1 Jul. 26, 2018

(30) Foreign Application Priority Data

Jan. 25, 2017 (JP) ................................ 2017-010910

(51) Int. Cl.
*C12Q 1/06* (2006.01)

(52) U.S. Cl.
CPC ........... *C12Q 1/06* (2013.01); *G01N 2333/37* (2013.01)

(58) Field of Classification Search
CPC ...................................................... C12Q 1/06
See application file for complete search history.

(56) References Cited

U.S. PATENT DOCUMENTS

| 2016/0355863 A1 | 12/2016 | Uriu |
| 2016/0355864 A1 | 12/2016 | Uriu |

FOREIGN PATENT DOCUMENTS

JP   2005-287337   10/2005

OTHER PUBLICATIONS

Cao et al. Ind. Eng. Chem. Res., 2006, 45:4193-4199.*
Candau et al. Applied and Environmental Microbiology, 1991, 57(11):3378-3382.*
Paul F. Morris et al., "Chemotropic and Contact Responses of Phytophthora sojae Hyphae to Soybean Isoflavonoids and Artificial Substrates", Plant Physiol. (1998) 117:1171-1178, Aug. 1, 1998.

* cited by examiner

*Primary Examiner* — Bin Shen
(74) *Attorney, Agent, or Firm* — McDermott Will & Emery LLP (57) ABSTRACT

The present invention provides a method for determining whether or not a test sample contains at least one phytopathogenic fungus selected from the group consisting of *Gibberella fujikuroi, Fusarium avenaceum*, and *Glomerella tucumanensis*. The method according to the present invention comprises: (a) putting the test sample on a front surface of a cellulose film; wherein the cellulose film has a thickness of not less than 0.5 micrometers and not more than 3.7 micrometers; (b) leaving the test sample at rest for not less than 4 hours and not more than 8 hours after the step (a); (c) observing a back surface of the film after the step (b); and (d) determining that the test sample contains at least one phytopathogenic fungus selected from the group consisting of *Gibberella fujikuroi, Fusarium avenaceum*, and *Glomerella tucumanensis*, if a fungus is found on the back surface of the film in the step (c).

13 Claims, 9 Drawing Sheets

--- Prior Art ---

FIG. 12

METHOD FOR DETERMINING WHETHER OR NOT TEST SAMPLE CONTAINS PHYTOPATHOGENIC FUNGUS

This application claims the benefit of foreign priority of Japanese patent application 2017-010910 filed on Jan. 25, 2017, the content of which is incorporated herein by reference.

BACKGROUND

1. Technical Field

The present invention relates to a method for determining whether or not a test sample contains a phytopathogenic fungus.

2. Description of the Related Art

Figure 12:
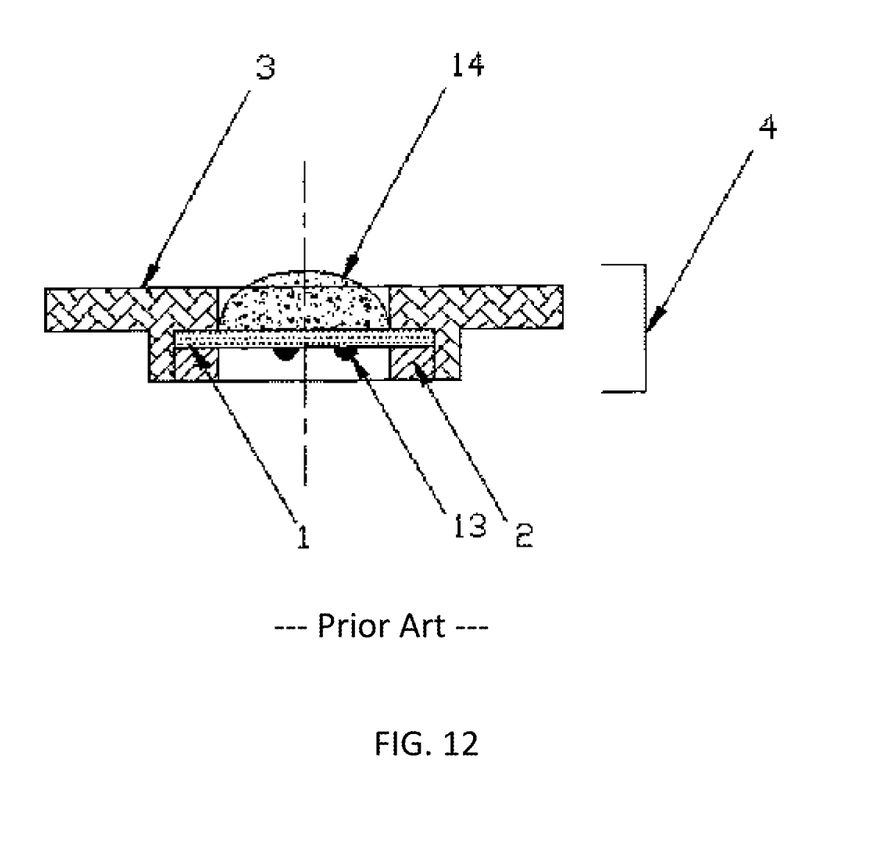
FIG. 12 shows a cross-sectional view of the microporous membrane supporting material used for the method for counting the number of mold cells disclosed in PTL1.

PTL1 discloses a method for counting the number of mold cells in a specimen by the culture for a short time and capable of accurately counting the cell number. FIG. 12 shows a cross-sectional view of a microporous membrane supporting material used for the method disclosed therein. According to this method, the extended multiple pseudomycelia of a mold cell 13 cultured by a liquid culture or a mold cell 13 cultured on a microporous membrane 1 of a microporous membrane supporting material 4 are photographed and the shape, area and luminous intensity are recognized and analyzed by an image analytic means 10. The number of the mold cells 13 can be counted by the culture for a short time. The microporous membrane 1 is interposed between a pressing ring 2 and a base 3.

NPL1 discloses that pseudohyphae of *Phytophthora sojae*, which is one of phytopathogenic oomycetes, penetrates the PET membrane having 3-micrometer pores.

CITATION LIST

Patent Literature

PTL1: Japanese Patent Application laid-open Publication No. 2005-287337A

Non-Patent Literature

NPL1: Paul F. Morris. et. al. "Chemotropic and Contact Responses of *Phytophthora sojae* Hyphae to Soybean Isoflavonoids and Artificial Substrates", Plant Physiol. (1998) 117: 1171-1178

SUMMARY

An object of the present invention is to provide a method for selectively determining whether or not a test sample contains at least one phytopathogenic fungus selected from the group consisting of *Gibberella fujikuroi, Fusarium avenaceum*, and *Glomerella tucumanensis*.

The present invention provides a method for determining whether or not a test sample contains at least one phytopathogenic fungus selected from the group consisting of *Gibberella fujikuroi, Fusarium avenaceum*, and *Glomerella tucumanensis*, the method comprising:

(a) putting the test sample on a front surface of a cellulose film;
wherein
the cellulose film has a thickness of not less than 0.5 micrometers and not more than 2 micrometers; and
the cellulose film has no through hole;
(b) leaving the test sample at rest for a predetermined time after the step (a);
(c) observing a back surface of the cellulose film after the step (b); and
(d) determining that the test sample contains the at least one phytopathogenic fungus selected from the group consisting of *Gibberella fujikuroi, Fusarium avenaceum*, and *Glomerella tucumanensis*, if a fungus which has penetrated the cellulose film is found on the back surface of the film in the step (c).

The present invention provides a method for selectively determining whether or not a test sample contains at least one phytopathogenic fungus selected from the group consisting of *Gibberella fujikuroi, Fusarium avenaceum*, and *Glomerella tucumanensis*.

DETAILED DESCRIPTION OF THE EMBODIMENT

First, a fungus will be described. Fungi are roughly divided into a phytopathogenic fungus and a non-phytopathogenic fungus. For example, the phytopathogenic fungus is a *Gibberella* genus, a *Fusarium* genus, or a *Glomerella* genus. An example of the phytopathogenic fungus is *Gibberella fujikuroi, Fusarium avenaceum*, or *Glomerella tucumanensis*. These phytopathogenic fungi cause root rot disease, blast, anthrax, or gray mold. These three phytopathogenic fungi kill the plant, especially, corn. An example of the non-phytopathogenic fungus is *Pythium catenulatum, Pythium torulosum* or *Pythium inflatum*.

The term "phytopathogenic" means to have pathogenicity to plants. The term "non-phytopathogenic" means not to have pathogenicity to plants. Even if a fungus has pathogenicity, however, if the fungus has no pathogenicity to plants, the fungus is non-phytopathogenic. In other words, if a fungus does not have adverse effects on plants, the fungus is non-phytopathogenic. The prefix "non-" included in the term "non-phytopathogenic" does not modify "phyto". The prefix "non-" modifies "pathogenic".

Hereinafter, the embodiment of the present invention will be described in more detail with reference to the drawings.

(Step (a))

In the step (a), a test sample is put on a front surface of a cellulose film having a thickness of not less than 0.5 micrometers and not more than 2 micrometers. The importance of the thickness of the cellulose film will be described later.

Figure 1:
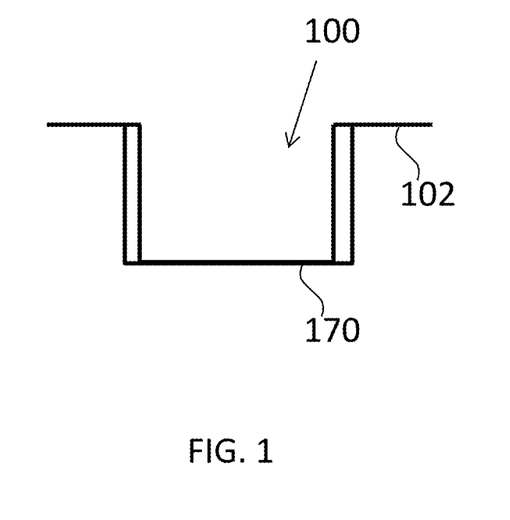
FIG. 1 shows a cross-sectional view of a first container.

In particular, as shown in FIG. 1, a container 100 is prepared. It is desirable that the container 100 comprises a flange 102 at the upper end thereof. The bottom surface of the container 100 is formed of a cellulose film 104. It is desirable that the cellulose film 104 is supported by a substrate (not shown in FIG. 1). This will be described later.

Figure 3:
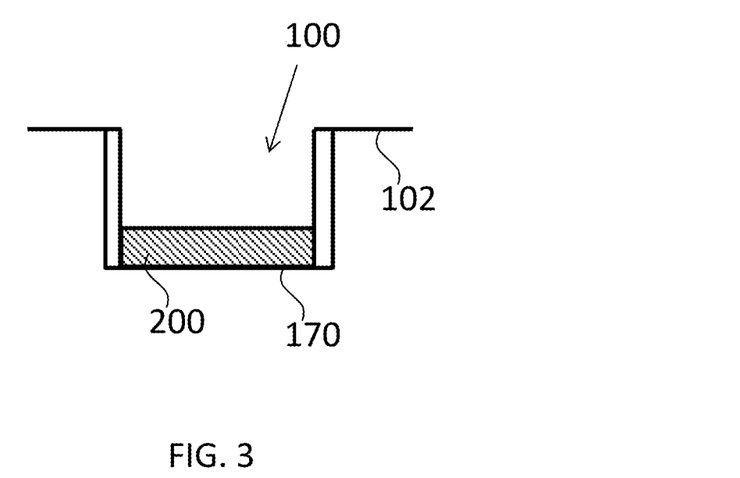
FIG. 3 shows a cross-sectional view of the first container to which a test sample has been supplied.
Figure 4:
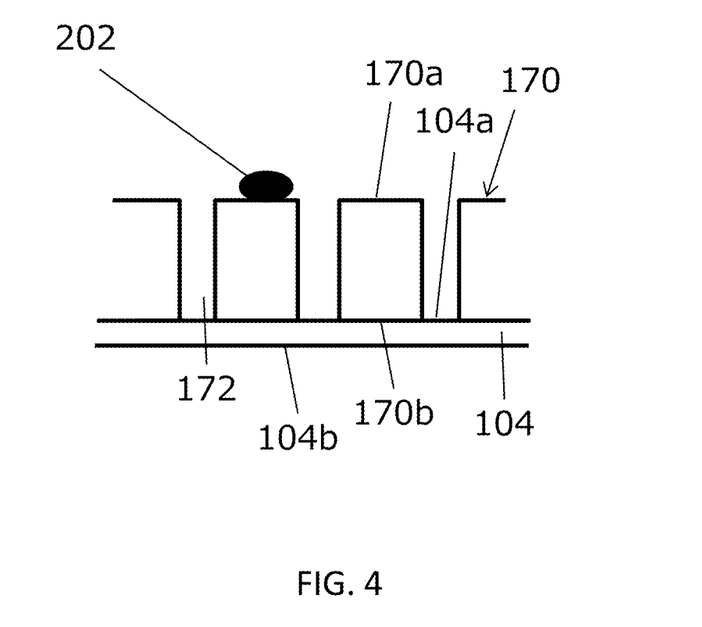
FIG. 4 shows a cross-sectional view of the cellulose film having a front surface on which a phytopathogenic fungus has been put.

As shown in FIG. 3, a test sample 200 is supplied to the inside of this container 100. In this way, the test sample 200 is put on a front surface 104a of the cellulose film 104. When the test sample 200 contains a phytopathogenic fungus 202, the phytopathogenic fungus 202 is put on the front surface 104a of the cellulose film 104, as shown in FIG. 4.

The test sample 200 is solid, liquid, or gaseous. It is desirable that the test sample 200 is solid or liquid. An example of the solid test sample 200 is soil or a crushed plant. Another example is an agricultural material such as vermiculite, rock wool or urethane. An example of the liquid test sample 200 is agricultural water, a solution used for hydroponic culture, a liquid used for washing a plant, a liquid extracted from a plant, a liquid used for washing an agricultural material, or a liquid used for washing clothing or shoes of a worker.

(Step (b))

In the step (b), the test sample 200 is left at rest for a certain incubation time after the step (a). An example of the incubation time is 24 hours. Hereinafter, the importance of the thickness of the cellulose film 104 will be described.

Figure 5:
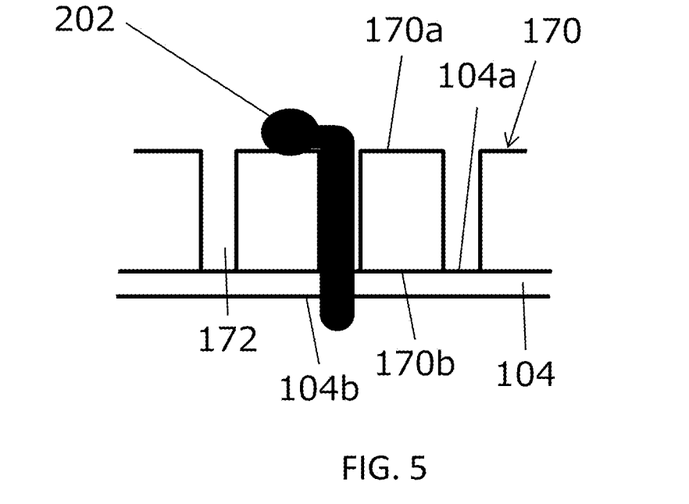
FIG. 5 is a cross-sectional view showing a state where the phytopathogenic fungus has penetrated the cellulose film.

In the step (b), various fungi contained in the test sample 200 are grown. As demonstrated in the experiments which will be described later, if the following requirement (I) is satisfied, the at least one phytopathogenic fungus 202 selected from the group consisting of *Gibberella fujikuroi*, *Fusarium avenaceum*, and *Glomerella tucumanensis* grows up so as to penetrate the cellulose film 104, as shown in FIG. 5. As a result, the phytopathogenic fungus 202 appears on a back surface 104b of the cellulose film 104.

Requirement (I): The cellulose film 104 has a thickness of not less than 0.5 micrometers and not more than 2 micrometers.

If the above requirement (I) is satisfied, a non-phytopathogenic fungus seldom penetrates the cellulose film 104. For this reason, the non-phytopathogenic fungus seldom appears on the back surface 104b of the cellulose film 104. In this way, the phytopathogenic fungus 202 appears on the back surface 104b selectively. In other words, the phytopathogenic fungus 202 appears outside of the container 100 selectively.

In case where the cellulose film 104 has a thickness of more than 2 micrometers, not only the non-phytopathogenic fungus but also the phytopathogenic fungus hardly penetrates the cellulose film 104 within the predetermined hours. Therefore, in case where the cellulose film 104 has a thickness of more than 2 micrometers, the selectivity is lost. In case where the cellulose film 104 has a thickness of less than 0.5 micrometers, not only the phytopathogenic fungus but also the non-phytopathogenic fungus penetrates the cellulose film 104 within the predetermined hours. Therefore, the selectivity is lost, in case where the cellulose film 104 has a thickness of less than 0.5 micrometers.

Figure 2:
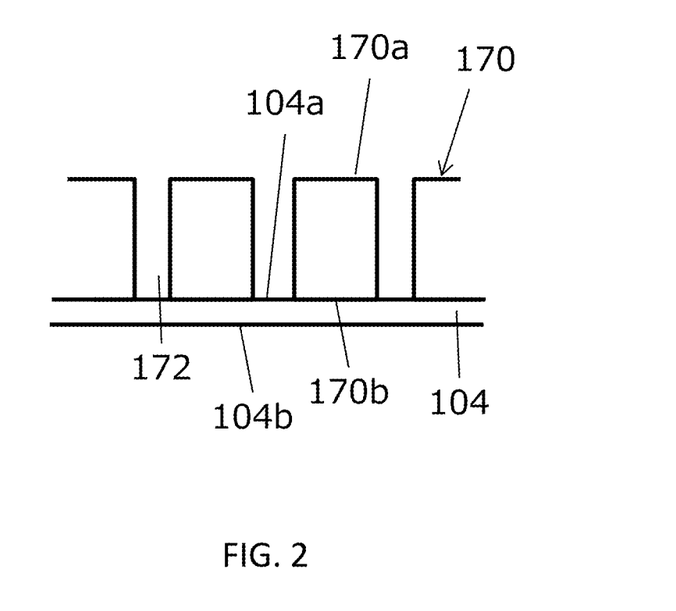
FIG. 2 shows a cross-sectional view of a cellulose film supported by a back surface of a substrate.

As shown in FIG. 2, the cellulose film 104 may comprise a substrate 170 comprising a through hole 172 on at least one of the front surface 104a and the back surface 104b thereof. In FIG. 2, the cellulose film 104 comprises the substrate 170 on the front surface thereof. In other words, in FIG. 2, the substrate 170 comprises the cellulose film 104 on a back surface 170b thereof. It is desirable that the through hole 172 has a diameter of not less than 3 micrometers. More desirably, the through hole 172 has a diameter of not less than 5 micrometers. In other words, it is desirable the through hole 172 has a cross-sectional area of not less than 7.065 square micrometers, more desirably, not less than 19.625 square micrometers. As one example, the through hole 172 has a diameter of not more than 8 micrometers. In other words, the through hole 172 may have a cross-sectional area of not more than 50.24 square micrometers. In case where the through hole 172 has a diameter of not more than 3 micrometers, the non-phytopathogenic fungus seldom reaches the inside of the through hole 172. As a result, the non-phytopathogenic fungus may fail to be brought into contact with the front surface of the cellulose film 104. For more detail, see United States Patent Application Publications No. 2016/0355863 and No. 2016/0355864, both of which are incorporated herein by reference.

Needless to say, as long as the cellulose film 104 is stretched taut, the substrate 170 is not required. In other words, if it is difficult to stretch the cellulose film 104 taut, the substrate 170 for supporting the cellulose film 104 is used. Unlike the substrate 170, note that the cellulose film 104 has no through hole.

A reference number 170a indicates the front surface of the substrate 170. As shown in FIG. 2, it is desirable that the substrate 170 has a plurality of through holes 172. The thickness of the substrate 170 is not limited; however, as one example, it is desirable that the substrate 170 has a thickness of not less than 1 micrometer and not more than 500 micrometers. The cellulose film 104 is significantly thin. However, if the cellulose film 104 is arranged on the substrate 170, it is easy to handle the cellulose film 104.

A culture medium may be supplied to the test sample 200 to accelerate the incubation of the fungus. In particular, a culture medium may be supplied to the inside of the container 100 containing the test sample 200. It is desirable that the culture medium is liquid. The culture medium may be supplied in the step (b). Alternatively, the culture medium may be supplied prior to the step (b). In other words, the culture medium may be supplied in the step (a). The culture medium may be supplied to the inside of the container 100 prior to the step (a).

Figure 6:
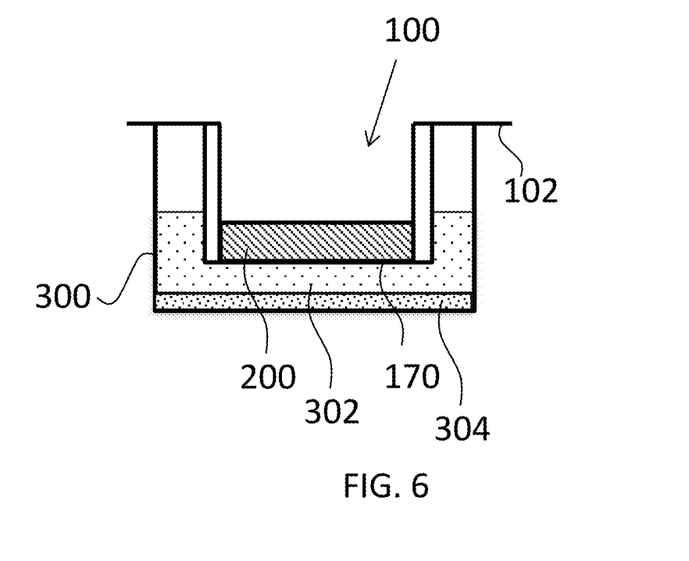
FIG. 6 shows a cross-sectional view of an example of a method for accelerating the incubation of the fungus.

FIG. 6 shows another method for accelerating the incubation of the fungus. As shown in FIG. 6, it is desirable that the back surface 104b of the cellulose film 104 is in contact with a liquid culture medium 302. First, a second container 300 having the liquid culture medium 302 therein is prepared. Hereinafter, the container 100 is referred to as "first container 100" to distinguish it from the second container 300. The first container 100 is stacked on the second container 300 in such a manner that the lower surface of the flange 102 is in contact with the upper end of the second container 300. In other words, the first container 100 is supported by the upper end of the second container 300. In this way, the liquid culture medium 302 is sandwiched between the back surface 104b of the cellulose film 104 and the bottom surface of the second container 300.

Alternatively, after the first container 100 is stacked on the second container 300, the liquid culture medium 302 may be supplied between the back surface 104b of the cellulose film 104 and the bottom surface of the second container 300.

In place of the liquid culture medium 302, a viscous solid culture medium may also be used. As shown in FIG. 6, both of a solid culture medium 304 and the liquid culture medium 302 may be used. In this case, the liquid culture medium 302 is sandwiched between the solid culture medium 304 and the cellulose film 104. As shown in FIG. 5, the incubation of the phytopathogenic fungus 202 which has appeared on the back surface 104b is accelerated by at least one of the liquid culture medium 302 and the solid culture medium 304.

(Step (c))

In the step (c), the back surface 104b of the cellulose film 104 is observed after the step (b). It is desirable that the back surface 104b is observed using an optical microscope.

The phytopathogenic fungus 202 appears on the back surface 104b of the cellulose film 104, as described in the step (b). On the other hand, the non-phytopathogenic fungus does not appear on the back surface 104b of the cellulose film 104. In this way, in the present invention, the phytopathogenic fungus 202 appears on the back surface 104b of the cellulose film 104 selectively.

In other words, the phytopathogenic fungus 202 penetrates the cellulose film 104, whereas the non-phytopathogenic fungus does not penetrate the cellulose film 104. For this reason, the non-phytopathogenic fungus does not appear on the back surface 104b of the cellulose film 104. In this way, the phytopathogenic fungus 202 appears on the back surface 104b selectively. In other words, the phytopathogenic fungus 202 appears outside of the first container 100 selectively.

In the step (c), it is observed whether or not the phytopathogenic fungus 202 appears on the back surface 104b of the cellulose film 104.

In particular, the back surface 104b of the cellulose film 104 is observed as below.

Figure 8:
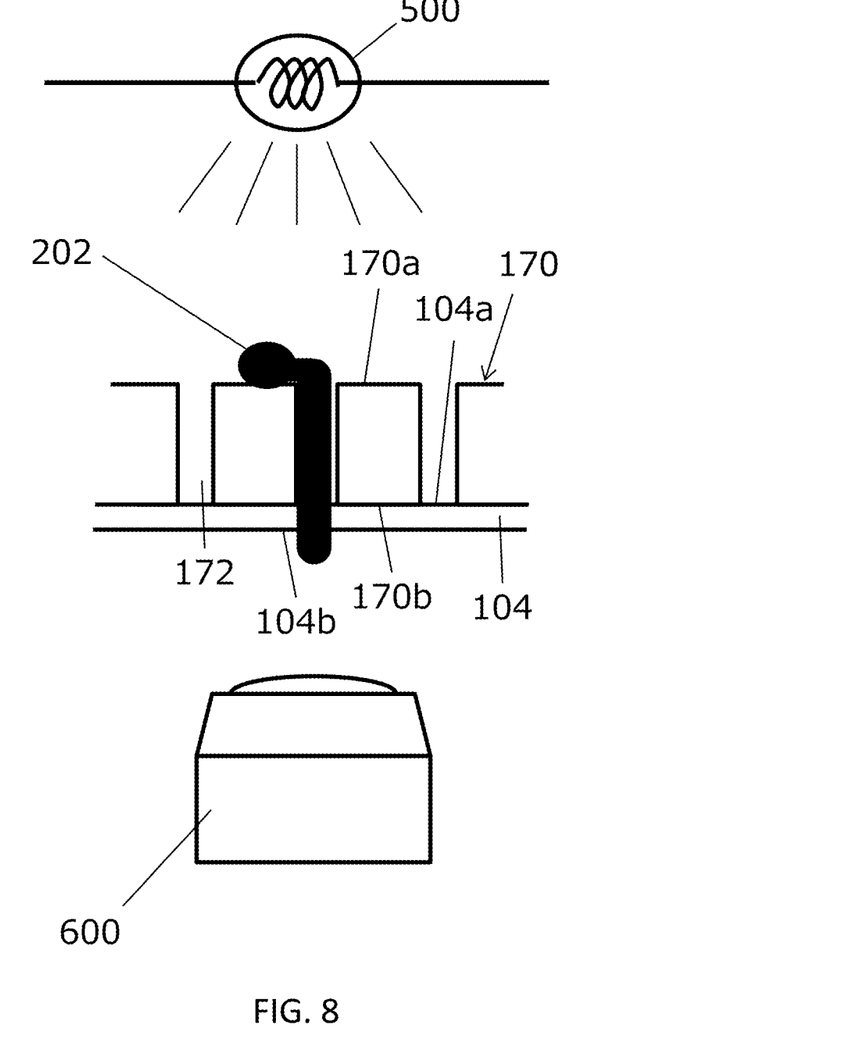
FIG. 8 is a cross-sectional view showing how to observe the fungus from the back surface of the cellulose film.

As shown in FIG. 8, while the cellulose film 104 is irradiated with light emitted from a light source 500 arranged above the front surface 104a of the cellulose film 104, the phytopathogenic fungus 202 is observed optically using a microscope 600 arranged below the back surface 104b of the cellulose film 104.

Figure 7:
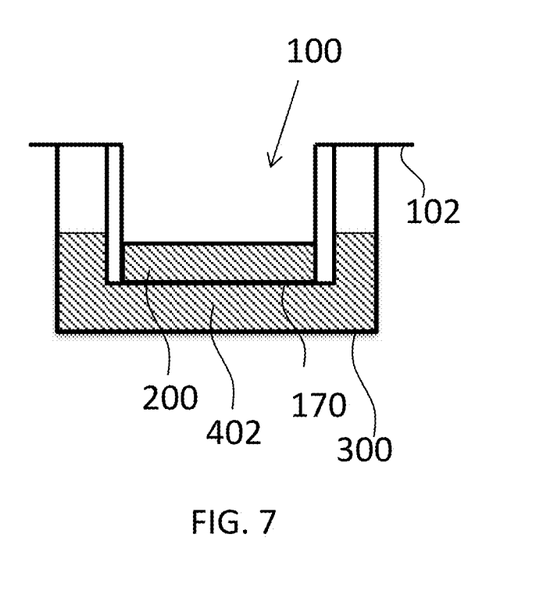
FIG. 7 shows a cross-sectional view, subsequently to FIG. 6, of the example of the method for accelerating the incubation of the fungus.

The liquid culture medium 302 and the solid culture medium 304 are removed from the second container 300. Then, a fluorescent agent having fungus combining ability is added to the inside of the second container 300. Hereinafter, such a fluorescent agent is referred to as "fungus fluorescent agent". The reference number of the fungus fluorescent agent is 402. Then, as shown in FIG. 7, the first container 100 is stacked on the second container 300 having the fungus fluorescent agent 402 therein. Alternatively, the fungus fluorescent agent 402 may be supplied between the back surface 104b of the cellulose film 104 and the bottom surface of the second container 300 after the first container 100 is stacked on the second container 300.

A part of the phytopathogenic fungus 202 which has appeared on the back surface 104b of the cellulose film 104 is dyed with the fungus fluorescent agent 402. Since the first container 100 is separated from the second container 300 by the cellulose film 104, the fungus fluorescent agent 402 does not spread into the first container 100. For this reason, the non-phytopathogenic fungus contained in the first container 100 is not dyed with the fungus fluorescent agent 402.

Figure 9:
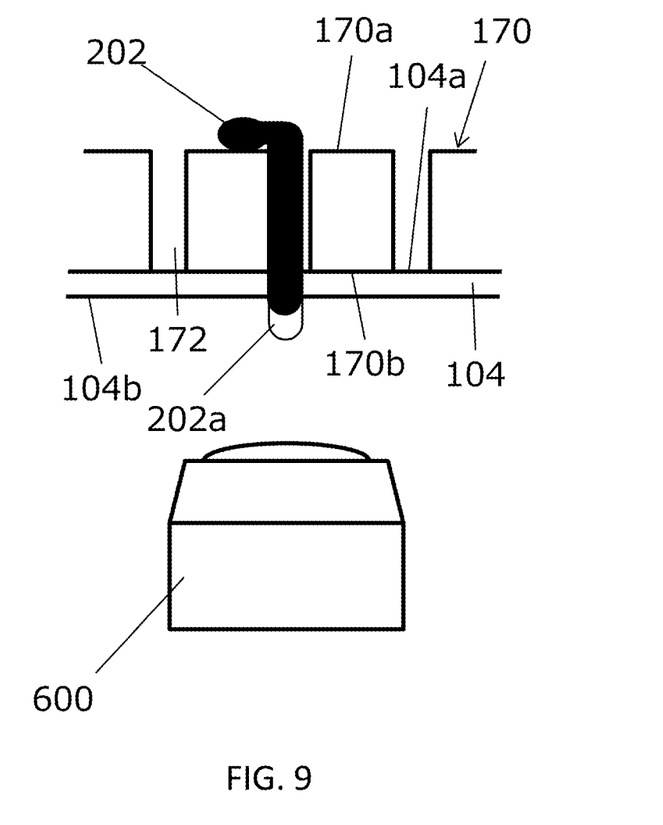
FIG. 9 is a cross-sectional view showing how to observe the fungus from the back surface of the cellulose film.
Figure 10:
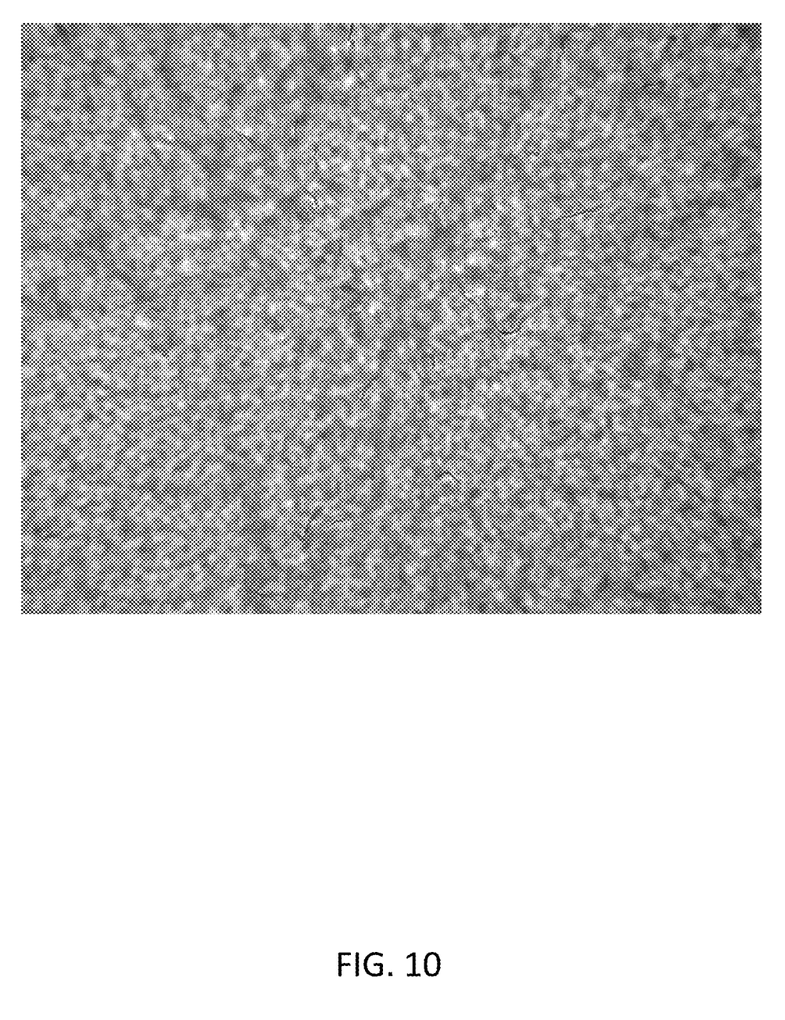
FIG. 10 is a microscope photograph of the back surface of the cellulose film in the inventive example 1A.
Figure 11:
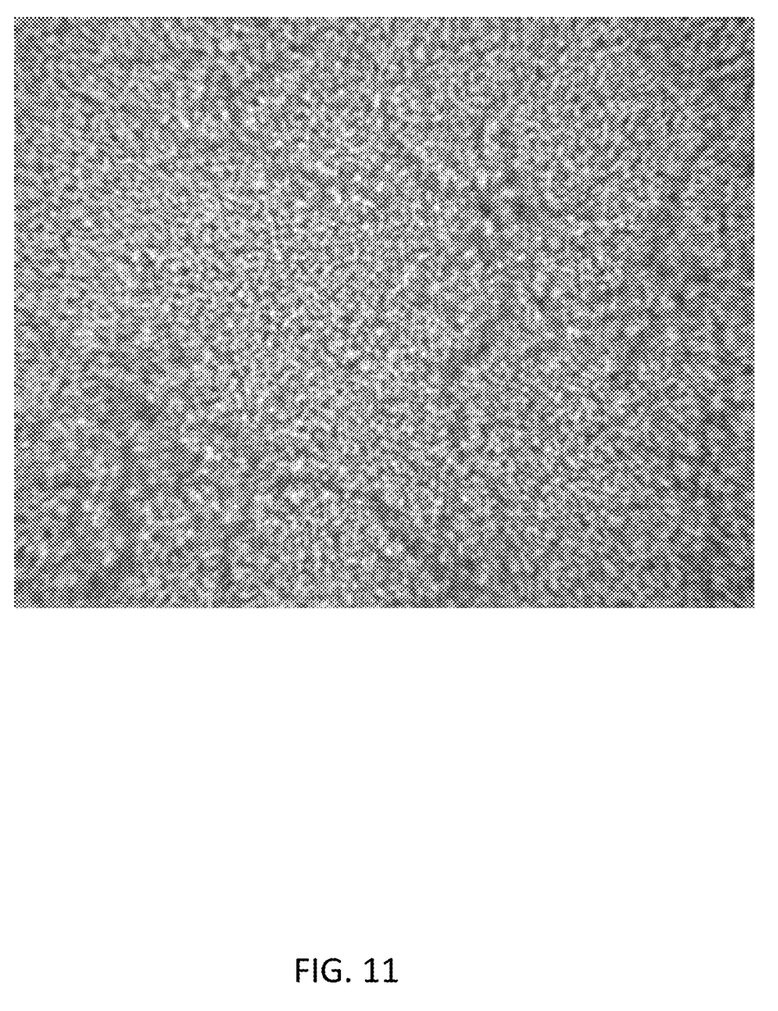
FIG. 11 is a microscope photograph of the back surface of the cellulose film in the comparative example 2A.

As shown in FIG. 9, the phytopathogenic fungus 202 dyed with the fungus fluorescent agent 402 is observed using the epifluorescence microscope 600 located under the back surface 104b of the cellulose film 104. Needless to say, the phytopathogenic fungus 202 may be observed without using the fungus fluorescent agent 402.

(Step (d))

In the step (d), it is determined that the test sample contains at least one phytopathogenic fungus selected from the group consisting of *Gibberella fujikuroi*, *Fusarium avenaceum*, and *Glomerella tucumanensis*, if a fungus is found on the back surface 104b of the cellulose film 104 in the step (c). Needless to say, it is determined that the test sample does not contain at least one phytopathogenic fungus selected from the group consisting of *Gibberella fujikuroi*, *Fusarium avenaceum*, and *Glomerella tucumanensis*, if a fungus is not found on the back surface 104b of the cellulose film 104 in the step (c).

EXAMPLES

The present invention will be described in more detail with reference to the following examples.

(Incubation of *Gibberella fujikuroi*)

*Gibberella fujikuroi*, one of the phytopathogenic fungi, was inoculated on a potato dextrose agar culture medium. Then, the culture medium was left at rest at a temperature of 25 degrees Celsius for one week. *Gibberella fujikuroi* was given by the National Bio-Resource Center (National Institute of Genetics, Mishima-city, Shizuoka, Japan)

Then, a part including ends of hyphae was cut together with the culture medium at a size of 1 centimeter×1 centimeter. The cut part was immersed in pure water disposed on a 12-well plate. Each of the pure water has a volume of 1 milliliter.

The water contained in the 12-well plate was observed using an optical microscope. As a result, the present inventors confirmed that spores of *Gibberella fujikuroi* were released in the water disposed on the 12-well plate. In this way, an aqueous solution containing *Gibberella fujikuroi* was provided. Hereinafter, this aqueous solution is referred to as "phytopathogenic fungus aqueous solution".

(Preparation of Culture Medium)

A potato dextrose culture medium having a volume of 650 microliters was added as the liquid culture medium 302 to the second container 300. In this way, the second container 300 containing the liquid culture medium 302 was prepared.

(Experiment 1)

The experiment 1 is composed of inventive examples 1A-1D, comparative examples 1E-1Z, and comparative examples 1AA-1AB.

Inventive Example 1A

The first container 100 shown in FIG. 1 was prepared as below.

First, cellulose (available from SIGMA-ALDRICH Co. LLC, trade name: Avicel PH-101) was dissolved in an ionic liquid to prepare a cellulose solution having a concentration of 2%. The ionic liquid was 1-butyl-3-methyl imidazolium chloride (available from SIGMA-ALDRICH Co. LLC).

The cellulose solution was warmed to 60 degrees Celsius. Then, the cellulose solution was applied by a spin coat method for thirty seconds at a rotation speed of 2,000 rpm onto a back surface of a container having a polyethylene terephthalate film on the bottom surface thereof (available from Merck KGaA, trade name: Millicell PISP 12R 48). The polyethylene terephthalate film served as the substrate 170. The polyethylene terephthalate film randomly had a plurality of through holes 172 each having a diameter of three micrometers. In this way, the cellulose film 104 having a thickness of 2.0 micrometers was formed on the back surface of the polyethylene terephthalate film.

The container was left at rest in ethanol at room temperature for 12 hours. In this way, 1-butyl-3-methyl imidazolium chloride was replaced with ethanol. In other words, 1-butyl-3-methyl imidazolium chloride was removed from the cellulose film 104.

Finally, the container was dried in a vacuum desiccator. In this way, the first container 100 shown in FIG. 1 was obtained. In FIG. 1, note that the polyethylene terephthalate film serving as the substrate 170 is not illustrated.

Then, as shown in FIG. 6, the first container 100 was stacked on the second container 300. The back surface 104*b* of the cellulose film 104 was in contact with the liquid culture medium 302. Subsequently, water having a volume of 200 microliters was added to the inside of the first container 100. Furthermore, the phytopathogenic fungus aqueous solution containing 200 spores of *Gibberella fujikuroi* was added to the inside of the first container 100.

The first container 100 was left at rest at a temperature of 25 degrees Celsius for 24 hours. In other words, in the inventive example 1A, the incubation time was 24 hours.

The number of the hyphae of *Gibberella fujikuroi* which appeared on the back surface 104*b* of the cellulose film 104 was counted visually with an optical microscope. The inventive example 1A was repeated fifteen times. FIG. 10 is a microscope photograph of the back surface 104*b* of the cellulose film 104 in the inventive example 1A.

Inventive Example 1B

In the inventive example 1B, an experiment similar to the inventive example 1A was conducted, except that each of the through holes 172 had a diameter of 5 micrometers. The container having a bottom surface comprising the through holes each having a diameter of 5 micrometers was available from Merck KGaA as a trade name: Millicell PIMP 12R 48.

Inventive Example 1C

In the inventive example 1C, an experiment similar to the inventive example 1A was conducted, except that each of the through holes 172 had a diameter of 8 micrometers. The container having a bottom surface comprising the through holes each having a diameter of 8 micrometers was available from Merck KGaA as a trade name: Millicell PIEP 12R 48.

Inventive Example 1D

In the inventive example 1D, an experiment similar to the inventive example 1A was conducted, except that the cellulose solution had a concentration of 1.0%, except that the cellulose film 104 had a thickness of 0.5 micrometers, and that each of the through hole 172 had a diameter of 3 micrometers.

Inventive Example 1E

In the inventive example 1E, an experiment similar to the inventive example 1A was conducted, except that the cellulose film 104 had a thickness of 0.5 micrometers, and that each of the through holes 172 had a diameter of 5 micrometer.

Inventive Example 1F

In the inventive example 1F, an experiment similar to the inventive example 1A was conducted, except that the cellulose film 104 had a thickness of 0.5 micrometers, and that each of the through holes 172 had a diameter of 8 micrometers.

Comparative Example 1G

In the comparative example 1G, an experiment similar to the inventive example 1A was conducted, except that the cellulose film 104 had a thickness of 4.4 micrometers (namely, the cellulose solution had a concentration of 4.0%) and that each of the through holes 172 had a diameter of 1 micrometer.

Comparative Example 1H

In the comparative example 1H, an experiment similar to the inventive example 1A was conducted, except that the cellulose film 104 had a thickness of 4.4 micrometers (namely, the cellulose solution had a concentration of 4.0%) and that each of the through holes 172 had a diameter of 3 micrometers.

Comparative Example 1I

In the comparative example 1I, an experiment similar to the inventive example 1A was conducted, except that the cellulose film 104 had a thickness of 4.4 micrometers (namely, the cellulose solution had a concentration of 4.0%) and that each of the through holes 172 had a diameter of 5 micrometers.

Comparative Example 1J

In the comparative example 1J, an experiment similar to the inventive example 1A was conducted, except that the cellulose film 104 had a thickness of 4.4 micrometers (namely, the cellulose solution had a concentration of 4.0%) and that each of the through holes 172 had a diameter of 8 micrometers.

Comparative Example 1K

In the comparative example 1K, an experiment similar to the inventive example 1A was conducted, except that the cellulose film 104 had a thickness of 3.7 micrometers (namely, the cellulose solution had a concentration of 3.0%) and that each of the through holes 172 had a diameter of 1 micrometer.

Comparative Example 1L

In the comparative example 1L, an experiment similar to the inventive example 1A was conducted, except that the cellulose film 104 had a thickness of 3.7 micrometers (namely, the cellulose solution had a concentration of 3.0%) and that each of the through holes 172 had a diameter of 3 micrometers.

Comparative Example 1M

In the comparative example 1M, an experiment similar to the inventive example 1A was conducted, except that the cellulose film 104 had a thickness of 3.7 micrometers (namely, the cellulose solution had a concentration of 3.0%) and that each of the through holes 172 had a diameter of 5 micrometers.

Comparative Example 1N

In the comparative example 1N, an experiment similar to the inventive example 1A was conducted, except that the cellulose film 104 had a thickness of 3.7 micrometers (namely, the cellulose solution had a concentration of 3.0%) and that each of the through holes 172 had a diameter of 8 micrometers.

Comparative Example 1O-1Z and 1AA-1AB

In the comparative examples 1O-1Z and 1AA-1AB, an experiment similar to the inventive example 1A was conducted in accordance with the disclosure shown in the following Table 1.

(Experiment 2)

In the experiment 2, a non-phytopathogenic fungus aqueous solution containing spores of *Saccharomyces cerevisiae* was used in place of the phytopathogenic fungus aqueous solution containing spores of *Gibberella fujikuroi*. Unlike *Gibberella fujikuroi*, *Saccharomyces cerevisiae* is one kind of non-phytopathogenic fungus. A non-phytopathogenic fungus aqueous solution containing spores of *Saccharomyces cerevisiae* was prepared similarly to the case of the phytopathogenic fungus aqueous solution containing spores of *Gibberella fujikuroi*. The experiment 2 is composed of comparative examples 2A-2Z and comparative examples 2AA-2AB.

Comparative Examples 2A-2Z and Comparative Examples 2AA-2AB

In the comparative examples 2A-2Z and 2AA-2AB, an experiment similar to the inventive example 1A was conducted in accordance with the disclosure shown in the following Table 2.

(Experiment 3)

In the experiment 3, a phytopathogenic fungus aqueous solution containing spores of *Fusarium avenaceum* was used in place of the phytopathogenic fungus aqueous solution containing spores of *Gibberella fujikuroi*. Similarly to *Gibberella fujikuroi*, *Fusarium avenaceum* is one kind of phytopathogenic fungus. A phytopathogenic fungus aqueous solution containing spores of *Fusarium avenaceum* was prepared similarly to the case of the phytopathogenic fungus aqueous solution containing spores of *Gibberella fujikuroi*. The experiment 3 is composed of inventive examples 3A-3F, comparative examples 3G-3Z and comparative examples 3AA-3AB.

Inventive Examples 3A-3F, Comparative Examples 3G-3Z and Comparative Examples 3AA-3AB In the inventive examples 3A-3F, the comparative examples 3G-3Z and 3AA-3AB, an experiment similar to the inventive example 1A was conducted in accordance with the disclosure shown in the following Table 3.

(Experiment 4)

In the experiment 4, a phytopathogenic fungus aqueous solution containing spores of *Glomerella tucumanensis* was used in place of the phytopathogenic fungus aqueous solution containing spores of *Gibberella fujikuroi*. Similarly to *Gibberella fujikuroi*, *Glomerella tucumanensis* is one kind of phytopathogenic fungus. A phytopathogenic fungus aqueous solution containing spores of *Glomerella tucumanensis* was prepared similarly to the case of the phytopathogenic fungus aqueous solution containing spores of *Gibberella fujikuroi*. The experiment 4 is composed of inventive examples 4A-4F, comparative examples 4G-4Z and comparative examples 4AA-4AB.

Inventive Examples 4A-4F, Comparative Examples 4G-4Z and Comparative Examples 4AA-4AB In the inventive examples 4A-4F, the comparative examples 4G-4Z and 4AA-4AB, an experiment similar to the inventive example 1A was conducted in accordance with the disclosure shown in the following Table 4.

(Experiment 5)

In the experiment 5, a non-phytopathogenic fungus aqueous solution containing spores of *Penicillium chysogeum* was used in place of the phytopathogenic fungus aqueous solution containing spores of *Gibberella fujikuroi*. Unlike *Gibberella fujikuroi*, *Penicillium chysogeum* is one kind of non-phytopathogenic fungus. A non-phytopathogenic fungus aqueous solution containing spores of *Penicillium chysogeum* was prepared similarly to the case of the phytopathogenic fungus aqueous solution containing spores of *Gibberella fujikuroi*. The experiment 5 is composed of comparative examples 5A-5Z and comparative examples 5AA-5AB.

Comparative Examples 5A-5Z and Comparative Examples 5AA-5AB

In the comparative example 5A-5Z and 5AA-5AB, an experiment similar to the inventive example 1A was conducted in accordance with the disclosure shown in the following Table 5.

The following Table 1-Table 5 show the number of the hyphae which penetrated the cellulose film 104 in the experiments.

TABLE 1

| | Film thickness ($\mu m$) | Diameter of Through hole ($\mu m$) | Name of Fungus | Number of hyphae which penetrated cellulose film 104 |
|---|---|---|---|---|
| C. example 1G | 4.4 | 1 | *Gibberella fujikuroi* (phytopathogenic) | 0 |
| C. example 1H | | 3 | | 0 |
| C. example 1I | | 5 | | 0 |
| C. example 1J | | 8 | | 0 |
| C. example 1K | 3.7 | 1 | | 0 |
| C. example 1L | | 3 | | 1 |
| C. example 1M | | 5 | | 9 |
| C. example 1N | | 8 | | 36.5 |
| C. example 1O | 2.0 | 1 | | 40.5 |
| I. example 1A | | 3 | | 7.2 |
| I. example 1B | | 5 | | 73 |
| I. example 1C | | 8 | | 112.5 |
| C. example 1P | 0.5 | 1 | | 123 |
| I. example 1D | | 3 | | 145 |
| I. example 1E | | 5 | | 118 |
| I. example 1F | | 8 | | 454.5 |
| C. example 1Q | 0.2 | 1 | | Null |
| C. example 1R | | 3 | | 68 |
| C. example 1S | | 5 | | 81.5 |
| C. example 1T | | 8 | | 397 |
| C. example 1U | 0.04 | 1 | | Null |
| C. example 1V | | 3 | | 221.5 |
| C. example 1W | | 5 | | 91.5 |

TABLE 1-continued

| Film thickness (μm) | Diameter of Through hole (μm) | Name of Fungus | Number of hyphae which penetrated cellulose film 104 |
|---|---|---|---|
| C. example 1X |  | 8 |  | >500 |
| C. example 1Y | 0 | 1 |  | 98.5 |
| C. example 1Z |  | 3 |  | >500 |
| C. example 1AA |  | 5 |  | >500 |
| C. example 1AB |  | 8 |  | >500 |

Incubation time: 24 hours
C.: Comparative
I.: Inventive

TABLE 2

| Film thickness (μm) | Diameter of Through hole (μm) | Name of Fungus | Number of hyphae which penetrated cellulose film 104 |
|---|---|---|---|
| C. example 2G | 4.4 | 1 | Saccharomyces cerevisiae (non-phytopathogenic) | 0 |
| C. example 2H |  | 3 |  | 0 |
| C. example 2I |  | 5 |  | 0 |
| C. example 2J |  | 8 |  | 0 |
| C. example 2K | 3.7 | 1 |  | 0 |
| C. example 2L |  | 3 |  | 0 |
| C. example 2M |  | 5 |  | 0 |
| C. example 2N |  | 8 |  | 0 |
| C. example 2O | 2.0 | 1 |  | 0 |
| I. example 2A |  | 3 |  | 0 |
| I. example 2B |  | 5 |  | 0 |
| C. example 2C |  | 8 |  | 0 |
| C. example 2P | 0.5 | 1 |  | 0 |
| C. example 2D |  | 3 |  | 0 |
| C. example 2E |  | 5 |  | 0 |
| C. example 2F |  | 8 |  | 0 |
| C. example 2Q | 0.2 | 1 |  | 0 |
| C. example 2R |  | 3 |  | 0 |
| C. example 2S |  | 5 |  | 0 |
| C. example 2T |  | 8 |  | 0 |
| C. example 2U | 0.04 | 1 |  | 0 |
| C. example 2V |  | 3 |  | 0 |
| C. example 2W |  | 5 |  | 0 |
| C. example 2X |  | 8 |  | 0 |
| C. example 2Y | 0 | 1 |  | 0 |
| C. example 2Z |  | 3 |  | 0 |
| C. example 2AA |  | 5 |  | 0 |
| C. example 2AB |  | 8 |  | 0 |

Incubation time: 24 hours
C.: Comparative
I.: Inventive

TABLE 3

| Film thickness (μm) | Diameter of Through hole (μm) | Name of Fungus | Number of hyphae which penetrated cellulose film 104 |
|---|---|---|---|
| C. example 3G | 4.4 | 1 | Fusarium avenaceum (phytopathogenic) | 0 |
| C. example 3H |  | 3 |  | 0 |
| C. example 3I |  | 5 |  | 0 |
| C. example 3J |  | 8 |  | 0 |
| C. example 3K | 3.7 | 1 |  | 0 |
| C. example 3L |  | 3 |  | 1 |
| C. example 3M |  | 5 |  | 11.5 |
| C. example 3N |  | 8 |  | 44.5 |
| C. example 3O | 2.0 | 1 |  | 0.5 |

TABLE 3-continued

| Film thickness (μm) | Diameter of Through hole (μm) | Name of Fungus | Number of hyphae which penetrated cellulose film 104 |
|---|---|---|---|
| I. example 3A |  | 3 |  | 19 |
| I. example 3B |  | 5 |  | 96 |
| I. example 3C |  | 8 |  | 161.5 |
| C. example 3P | 0.5 | 1 |  | 18 |
| I. example 3D |  | 3 |  | 136 |
| I. example 3E |  | 5 |  | 134 |
| I. example 3F |  | 8 |  | 236.5 |
| C. example 3Q | 0.2 | 1 |  | Null |
| C. example 3R |  | 3 |  | 208.5 |
| C. example 3S |  | 5 |  | 208 |
| C. example 3T |  | 8 |  | 136 |
| C. example 3U | 0.04 | 1 |  | Null |
| C. example 3V |  | 3 |  | >500 |
| C. example 3W |  | 5 |  | >500 |
| C. example 3X |  | 8 |  | 136 |
| C. example 3Y | 0 | 1 |  | 14 |
| C. example 3Z |  | 3 |  | 216.5 |
| C. example 3AA |  | 5 |  | 110.5 |
| C. example 3AB |  | 8 |  | 85.5 |

Incubation time: 24 hours
C.: Comparative
I.: Inventive

TABLE 4

| Film thickness (μm) | Diameter of Through hole (μm) | Name of Fungus | Number of hyphae which penetrated cellulose film 104 |
|---|---|---|---|
| C. example 4G | 4.4 | 1 | Glomerella tucumanensis (phytopathogenic) | 0 |
| C. example 4H |  | 3 |  | 0 |
| C. example 4I |  | 5 |  | 0 |
| C. example 4J |  | 8 |  | 3 |
| C. example 4K | 3.7 | 1 |  | 0 |
| C. example 4L |  | 3 |  | 3 |
| C. example 4M |  | 5 |  | 4.5 |
| C. example 4N |  | 8 |  | 33 |
| C. example 4O | 2.0 | 1 |  | 0 |
| I. example 4A |  | 3 |  | 72 |
| I. example 4B |  | 5 |  | 66 |
| I. example 4C |  | 8 |  | 67 |
| C. example 4P | 0.5 | 1 |  | 0 |
| I. example 4D |  | 3 |  | 80 |
| I. example 4E |  | 5 |  | 79 |
| I. example 4F |  | 8 |  | 93.5 |
| C. example 4Q | 0.2 | 1 |  | Null |
| C. example 4R |  | 3 |  | 8.5 |
| C. example 4S |  | 5 |  | 20.5 |
| C. example 4T |  | 8 |  | 123 |
| C. example 4U | 0.04 | 1 |  | Null |
| C. example 4V |  | 3 |  | 30 |
| C. example 4W |  | 5 |  | 35 |
| C. example 4X |  | 8 |  | 98 |
| C. example 4Y | 0 | 1 |  | 1.5 |
| C. example 4Z |  | 3 |  | 58.5 |
| C. example 4AA |  | 5 |  | 56.5 |
| C. example 4AB |  | 8 |  | 3.5 |

Incubation time: 24 hours
C.: Comparative
I.: Inventive

TABLE 5

| | Film thickness (μm) | Diameter of Through hole (μm) | Name of Fungus | Number of hyphae which penetrated cellulose film 104 |
|---|---|---|---|---|
| C. example 5G | 4.4 | 1 | Penicillium chysogeum (non-phytopathogenic) | 0 |
| C. example 5H | | 3 | | 0 |
| C. example 5I | | 5 | | 0 |
| C. example 5J | | 8 | | 0 |
| C. example 5K | 3.7 | 1 | | 0 |
| C. example 5L | | 3 | | 0 |
| C. example 5M | | 5 | | 0 |
| C. example 5N | | 8 | | 0 |
| C. example 5O | 2 | 1 | | 0 |
| C. example 5A | | 3 | | 0 |
| C. example 5B | | 5 | | 0 |
| C. example 5C | | 8 | | 0 |
| C. example 5P | 0.5 | 1 | | 0 |
| C. example 5D | | 3 | | 0 |
| C. example 5E | | 5 | | 0 |
| C. example 5F | | 8 | | 6.8 |
| C. example 5Q | 0.2 | 1 | | 0 |
| C. example 5R | | 3 | | 110.5 |
| C. example 5S | | 5 | | 98.5 |
| C. example 5T | | 8 | | 54 |
| C. example 5U | 0.04 | 1 | | 0 |
| C. example 5V | | 3 | | 112.5 |
| C. example 5W | | 5 | | 59.5 |
| C. example 5X | | 8 | | 21 |
| C. example 5Y | 0 | 1 | | 0 |
| C. example 5Z | | 3 | | 10 |
| C. example 5AA | | 5 | | 11.7 |
| C. example 5AB | | 8 | | 4.3 |

Incubation time: 24 hours
C.: Comparative
I.: Inventive

The comparative examples 1Q, 1U, 3Q, 3U, 4Q, and 4U were not conducted actually.

As is clear from Table 1-Table 5, when the following requirement (I) is satisfied, the corn phytopathogenic fungus appears on the back surface 104b of the cellulose film 104 selectively. In other words, the corn phytopathogenic fungus 202 appears outside of the container 100 selectively.

Requirement (I): The cellulose film 104 has a thickness of not less than 0.5 micrometers and not more than 2 micrometers.

As demonstrated in the inventive example 1A, the number of hyphae which penetrated cellulose film 104 is 7.2 at a minimum, as long as the requirement (I) is satisfied. On the other hand, as long as the requirement (I) is satisfied, the non-phytopathogenic fungus hardly penetrates the cellulose film 104. As demonstrated in the comparative example 5F, the number of hyphae which penetrated cellulose film 104 is 6.8 at a maximum, when the requirement (I) is satisfied.

INDUSTRIAL APPLICABILITY

The present invention can be used to determine easily whether or not a test sample such as agricultural water or soil contains at least one phytopathogenic fungus selected from the group consisting of Gibberella fujikuroi, Fusarium avenaceum, and Glomerella tucumanensis.

REFERENCE SIGNS LIST

100 First container
  102 Flange
  104 Cellulose film
    104a Front surface
    104b Back surface
170 Substrate
  170a Front surface
  170b Back surface
200 Test sample
  202 Phytopathogenic fungus
    202a Part of Phytopathogenic fungus
  300 Second container
    302 Liquid culture medium
    304 Solid culture medium
  402 Fluorescent agent having fungus combining ability
  500 Light source
  600 Microscope

The invention claimed is:

1. A method for determining whether or not a test sample contains at least one phytopathogenic fungus selected from the group consisting of Gibberella fujikuroi, Fusarium avenaceum, and Glomerella tucumanensis, the method comprising:
    (a) putting the test sample on a front surface of a cellulose film forming a portion of a bottom of a container:
    wherein the cellulose film has a thickness of not less than 0.5 micrometers and not more than 2 micrometers; and
    the cellulose film has no through hole;
    (b) incubating the test sample at room temperature for a predetermined time after step (a);
    (c) inspecting and quantifying a back surface of the cellulose film outside of the container after step (b) for fungi hyphae; and
    (d) identifying from the test sample at least one phytopathogenic fungus selected from the group consisting of Gibberella fujikuroi, Fusarium avenaceum, and Glomerella tucumanensis, if a fungus which has penetrated the cellulose film is found on the back surface of the film in step (c),
    wherein the predetermined time is greater than or equal to 24 hours,
    the back surface of the cellulose film is an external surface of the container,
    the cellulose film is supported by a substrate provided on at least one of the front surface and the back surface of the cellulose film; and
    the substrate comprises a through hole having a diameter within a range from three micrometers to eight micrometers.

2. The method according to claim 1, further comprising:
    a step of bringing the back surface of the cellulose film into contact with a fluorescent agent having fungus combining ability between the step (b) and the step (c).

3. The method according to claim 1, further comprising:
    a step of supplying a culture medium to the test sample before the step (b).

4. The method according to claim 3, wherein the culture medium is a liquid culture medium.

5. The method according to claim 3, wherein the culture medium is a solid culture medium.

6. The method according to claim 1, wherein the test sample is left at rest while the back surface of the cellulose film is in contact with the culture medium in the step (b).

7. The method according to claim 6, wherein the culture medium is a liquid culture medium.

8. The method according to claim 6, wherein the culture medium is a solid culture medium.

9. The method according to claim 1, wherein the through hole has a diameter of not less than five micrometers.

10. The method according to claim 1, wherein the test sample is solid.

11. The method according to claim 10, wherein the solid test sample is at least one selected from the group consisting of soil and a crushed plant.

12. The method according to claim 1, wherein the test sample is liquid.

13. The method according to claim 12, wherein the liquid test sample is at least one selected from the group consisting of agricultural water, a liquid used for hydroponic culture, a liquid used for washing a plant, a liquid extracted from a plant, a liquid used for washing an agricultural material, and a liquid used for washing clothing or a shoe.

* * * * *